US009204788B2

(12) United States Patent
Yu et al.

(10) Patent No.: US 9,204,788 B2
(45) Date of Patent: Dec. 8, 2015

(54) AUTOFOCUS METHOD USING LIQUID LENS (75) Inventors: Zaiguang Yu, Pudong (CN); Guijian Wang, Pudong (CN); Zhaohua Liu, YangPu (CN)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 14/003,261

(22) PCT Filed: Mar. 14, 2012

(86) PCT No.: PCT/CN2012/072302
§ 371 (c)(1),
(2), (4) Date: Sep. 5, 2013

(87) PCT Pub. No.: WO2012/126324
PCT Pub. Date: Sep. 27, 2012

(65) Prior Publication Data
US 2014/0002626 A1 Jan. 2, 2014

Related U.S. Application Data (60) Provisional application No. 61/454,651, filed on Mar. 21, 2011.

(51) Int. Cl.
*H04N 7/18* (2006.01)
*A61B 1/045* (2006.01)
(Continued)

(52) U.S. Cl.
CPC ............... *A61B 1/045* (2013.01); *A61B 1/0019* (2013.01); *A61B 1/04* (2013.01); *A61B 1/24* (2013.01); *A61B 1/247* (2013.01); *G02B 3/14* (2013.01); *G02B 7/285* (2013.01); *G03B 3/10* (2013.01);
(Continued)

(58) Field of Classification Search
CPC ........ A61B 1/045; A61B 1/0019; A61B 1/04; A61B 1/247; A61B 1/24; G02B 7/285; G02B 3/14; G02B 3/10; H04N 5/23212; H04N 2005/2255
USPC .............................................. 348/66; 351/233
See application file for complete search history.

(56) References Cited

U.S. PATENT DOCUMENTS 3,599,548 A   8/1971  Hennig
4,199,425 A   4/1980  Sinkevitch
(Continued)

FOREIGN PATENT DOCUMENTS

CN   1510498   7/2004
CN   1720466   1/2006
(Continued)

OTHER PUBLICATIONS

International Search Report completed Jun. 28, 2012 for International Application No. PCT/CN12/72302, 3 Pages.
(Continued)

*Primary Examiner* — Allen Wong (57) ABSTRACT

An autofocus method for an intra-oral camera modulates the focus of a liquid lens in a cycle that has at least first, second, and third focus positions and obtains an image at each focus position, measuring focus of the obtained image. The position of the liquid lens is adjusted according to the measured focus. Steps of modulating the focus of the liquid lens in the cycle with at least first, second, and third focus positions, and obtaining the image at each focus position and measuring focus of the obtained image are repeated.

9 Claims, 10 Drawing Sheets (51) Int. Cl.
*A61B 1/00* (2006.01)
*A61B 1/04* (2006.01)
*A61B 1/247* (2006.01)
*G02B 7/28* (2006.01)
*G02B 3/14* (2006.01)
*G03B 3/10* (2006.01)
*H04N 5/232* (2006.01)
*A61B 1/24* (2006.01)
*H04N 5/225* (2006.01)

(52) U.S. Cl.
CPC .... *H04N 5/23212* (2013.01); *H04N 2005/2255* (2013.01)

(56) References Cited

U.S. PATENT DOCUMENTS

| | | | |
|---|---|---|---|
| 4,947,245 A * | 8/1990 | Ogawa et al. | 348/66 |
| 4,998,809 A | 3/1991 | Tsuji et al. | |
| 5,040,881 A | 8/1991 | Tsuji | |
| 5,923,908 A | 7/1999 | Schrock et al. | |
| 6,019,721 A | 2/2000 | Holmes et al. | |
| 6,369,954 B1 | 4/2002 | Berge et al. | |
| 6,449,081 B1 | 9/2002 | Onuki et al. | |
| 7,010,223 B2 | 3/2006 | Thoms | |
| 7,027,094 B2 | 4/2006 | Battles et al. | |
| 7,245,440 B2 | 7/2007 | Peseux | |
| 7,656,588 B2 | 2/2010 | Bae et al. | |
| 7,801,589 B2 | 9/2010 | Tanikawa et al. | |
| 7,808,717 B2 | 10/2010 | Kuiper et al. | |
| 7,852,454 B2 | 12/2010 | Border et al. | |
| 2002/0013532 A1 * | 1/2002 | Czubko et al. | 600/478 |
| 2005/0168579 A1 | 8/2005 | Imamura | |
| 2006/0079728 A1 | 4/2006 | Kuiper et al. | |
| 2006/0166162 A1 | 7/2006 | Ting | |
| 2007/0139785 A1 | 6/2007 | Kuiper et al. | |
| 2007/0156021 A1 * | 7/2007 | Morse et al. | 600/167 |
| 2007/0236802 A1 * | 10/2007 | Kohno | 359/665 |
| 2008/0079897 A1 | 4/2008 | Goldfain et al. | |
| 2008/0266521 A1 * | 10/2008 | Campbell | 351/233 |
| 2009/0141352 A1 | 6/2009 | Jannard et al. | |
| 2011/0267520 A1 * | 11/2011 | Pyanet et al. | 348/296 |
| 2011/0298892 A1 * | 12/2011 | Baer | 348/46 |

FOREIGN PATENT DOCUMENTS

| | | |
|---|---|---|
| CN | 1916669 | 2/2007 |
| CN | 101313840 | 12/2008 |
| CN | 101331417 | 12/2008 |
| CN | 101510041 | 8/2009 |
| CN | 101822526 | 9/2010 |
| CN | 101896850 | 11/2010 |
| DE | 10125772 | 12/1992 |
| DE | 102008031054 | 7/2009 |
| DE | 102009017801 | 10/2010 |
| EP | 1780575 | 5/2007 |
| EP | 2071367 | 6/2009 |
| EP | 2161607 | 3/2010 |
| JP | S6236632 A | 2/1987 |
| JP | 11-084219 | 3/1999 |
| JP | 2004-219546 | 8/2004 |
| JP | 2006/509263 | 3/2006 |
| JP | 2006-215327 | 8/2006 |
| JP | 2006-324879 | 11/2006 |
| JP | 2007/167387 | 7/2007 |
| JP | 2007-206325 | 8/2007 |
| JP | 2007-538338 | 12/2007 |
| JP | 2008-80117 | 4/2008 |
| WO | WO2004084262 | 9/2004 |
| WO | WO2005/116908 | 12/2005 |
| WO | 2007/080521 | 7/2007 |
| WO | WO2007/088454 | 8/2007 |
| WO | WO2008/013181 | 1/2008 |
| WO | WO2008/048402 | 4/2008 |
| WO | WO2010/057336 | 5/2010 |

OTHER PUBLICATIONS

International Search Report completed Jul. 16, 2010 for International Application No. PCT/CN09/01208, 3 Pages.
Supplementary EP Search Report completed May 17, 2013 for European Patent Application No. 09850703, 2 Pages.
International Search Report completed Feb. 2, 2012 for International Application No. PCT/CN11/00606, 4 Pages.
International Search Report completed Aug. 17, 2009 for International Application No. PCT/CN08/01900, 4 Pages.
European Search Report mailed Aug. 28, 2014 for European Patent Application No. 12 760 604.4, 2 pages.

* cited by examiner

AUTOFOCUS METHOD USING LIQUID LENS

CROSS REFERENCE TO RELATED APPLICATIONS

This application claims the benefit of and is a US national phase filing of PCT application No. PCT/CN2012/072302 filed Mar. 14, 2012 that is entitled "AUTOFOCUS METHOD USING LIQUID LENS" in the names of Zaiguang Yu, Guijian Wang and Zhaohua Liu; which itself claims benefit of Provisional application U.S. Ser. No. 61/454,651, provisionally filed on Mar. 21, 2011 that is entitled "AN AUTO-FOCUS METHOD USING LIQUID LENS" in the names of Zaiguang Yu, Guijian Wang and Zhaohua Liu; the disclosures of both priority applications are incorporated herein by reference in their entirety.

FIELD OF THE INVENTION

The invention relates generally to apparatus for dental imaging. More specifically, the invention relates to autofocus methods for an intra-oral camera having a liquid lens.

BACKGROUND OF THE INVENTION

While there have been improvements in detection, treatment and prevention techniques, dental caries remains a prevalent condition affecting people of all age groups. If not properly and promptly treated, caries could lead to permanent tooth damage and even to loss of teeth. Thus dental imaging based on an intra-oral camera is of great interest.

There exist known intra-oral cameras, such as those available from ACTEON Inc. of Mount Laurel, N.J., USA. Generally, intra-oral cameras are operated over a large working distance range that typically varies between about 1 mm to about 50 mm. They must also have a sizable depth of field (DOF), which is different at different working distances. Thus, focus adjustment is necessary to provide good image quality. However, for most of the known intra-oral cameras including the one disclosed in U.S. Pat. No. 6,019,721 (Holmes et al.), focus adjustment is performed manually by operator adjustment to the distance between a lens and an imaging sensor. Conventional intra-oral cameras must be separately adjusted for each image. This makes these conventional cameras poorly suited for obtaining images in the dental office and practitioners can find cameras without an autofocus capability more difficult to use.

System optics for intra-oral cameras must provide a large depth of field (DOF) and as wide a field of view (FOV) as is possible. Some of the existing intraoral camera use a small NA (numerical aperture) that can provide sufficient DOF (depth of field) to help reduce the requirements for focus adjustment. However, an optical system having a small NA has limitations and is poorly suited for providing the high resolution needed for dental examination. The small NA can be unable to provide sufficient luminous flux for intra-oral use.

A number of solutions that have been proposed for intraoral imaging use a liquid lens as part of the imaging optics. The liquid lens can adjust more readily to intraoral requirements and is advantaged with respect to FOV and DOF. Autofocus, however, remains a problem. Accordingly, there is a need to provide an intraoral camera having an auto focus capability that does not require additional components and that operates quickly enough for use in the dental office.

SUMMARY OF THE INVENTION

An object of the present invention is to provide an intra-oral camera having a liquid lens and capable of providing autofocus. Embodiments of the present invention are advantaged for providing a camera that is compact, provides suitable imaging, and does not require focus by the operator or practitioner.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided an autofocus method for an intra-oral camera comprising:

modulating the focus of a liquid lens in a cycle that has at least first, second, and third focus positions;

obtaining an image at each focus position and measuring focus of the obtained image;

adjusting lens position according to the measured focus; and     repeating steps of modulating the focus of the liquid lens in the cycle with at least first, second, and third focus positions, and obtaining the image at each focus position and measuring focus of the obtained image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Where they are used, the terms "first", "second", "third", and so on, do not necessarily denote any ordinal or priority relation, but may be used for more clearly distinguishing one element or time interval from another.

Figure 1:
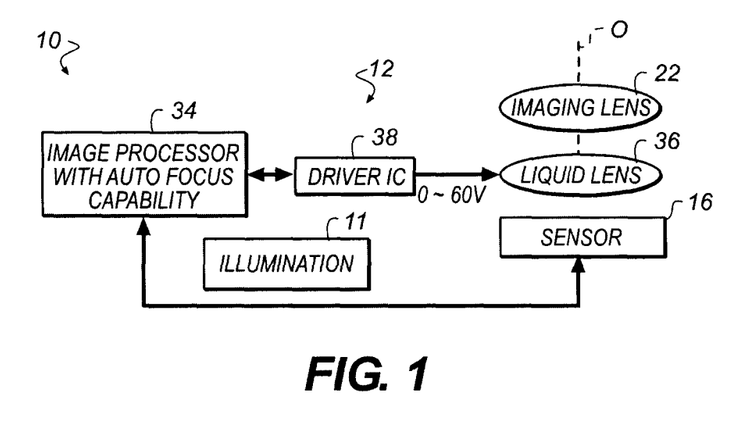
FIG. 1 shows a schematic view of components of an intra-oral camera of the present invention.

FIG. 1 shows components of an intra-oral camera 10 of the present invention according to one embodiment. Intra-oral camera 10 comprises an illumination system 11, an imaging system 12, and an imaging sensor 16. Imaging system 12 includes a liquid lens 36 having multiple electrodes, liquid lens driver element 38, and a microprocessor 34. Intra-oral camera 10 is intended for imaging a target tooth or other structure that is within the mouth of a patient, and to do this expediently and accurately.

Imaging system 12 provides a large depth of field (DOF) and forms an image of the target onto sensor 16. Liquid lens 36 in cooperation with an imaging lens 22 allows focus of imaging system 12 without the need for adjustment by an operator. The liquid lens that is used provides an adjustable lens element disposed at a position along the optical path, optical axis O, and actuable to change refraction with respect to each of two orthogonal axes in response to received adjustment signals from driver element 38. The position of the liquid lens along the optical axis O is also adjustable, with its linear position along the optical axis O also controlled by driver element 38. The use of this type of adjustable lens differentiates intra-oral camera 10 of the present invention from conventional intra-oral cameras and from many other types of conventional cameras that are intended for other uses.

Figure 2A:
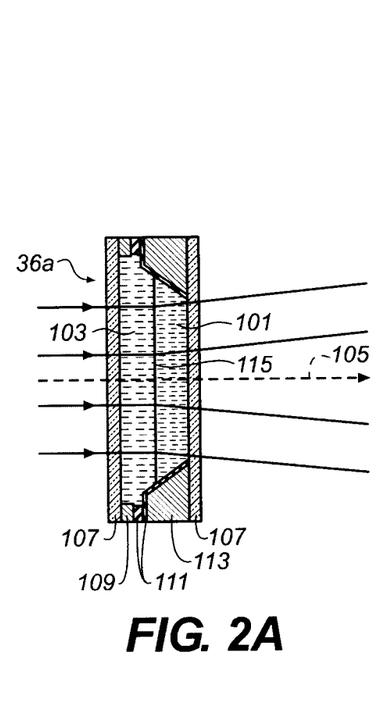
FIG. 2A is a side view schematic diagram that shows a liquid lens in a zero voltage state.
Figure 2B:
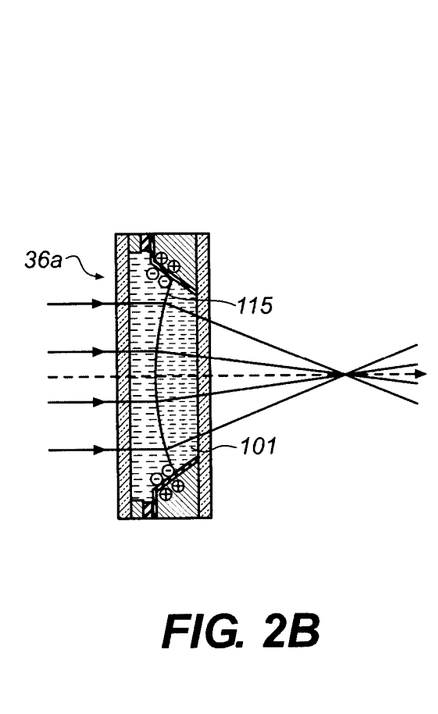
FIG. 2B is a side view schematic diagram that shows the two-electrode liquid lens with a non-zero applied voltage.
Figure 2C:
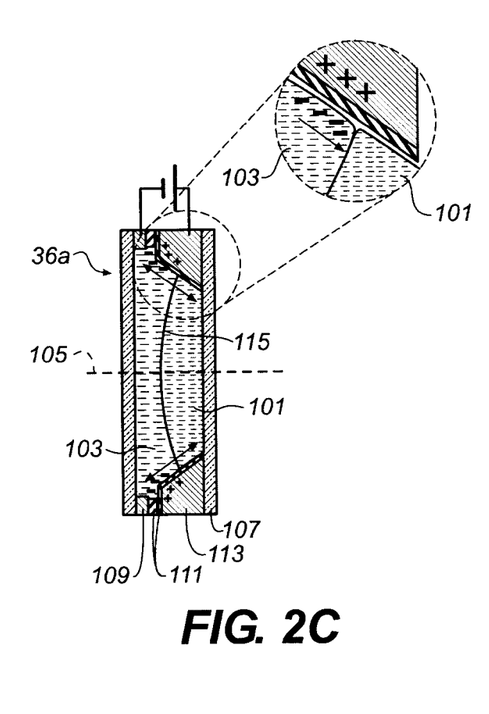
FIG. 2C is a side view schematic diagram that shows working principles of the two-electrode liquid lens.

In order to better understand how embodiments of the present invention are advantaged over camera embodiments using conventional liquid lenses, it is useful to review how the liquid lens operates. Referring to FIGS. 2A-2C, a conventional liquid lens 36a generally includes two kinds of liquids of equal density. The liquids are sandwiched between two transparent windows 107 in a conical vessel. In one embodiment, one liquid is conductive water 103, while the other is oil 101 for providing a measure of stability for the optical axis 105. Liquid lens 36a further includes electrodes 109 and 113 insulated from oil 101 but in electrical contact with water 103; and variable voltage can be selectively applied to the electrodes as an adjustment signal. An insulator 111 is deposited between electrodes 109 and 113 to separate them. The interface 115 between oil 101 and water 103 changes its shape depending on the voltage applied across the conical structure. As shown in FIG. 2A, when zero volts are applied, interface 115 is slightly curved and the surface of oil 101 becomes slightly concave. When the voltage is increased to about 40 volts, the surface of oil 101 becomes highly convex, as shown in FIG. 2B. In this way, liquid lens 36a can attain the desired refraction power by means of changing the voltage applied on the electrodes.

FIG. 2C summarizes the working principle of liquid lens 36a having two electrodes 109 and 113. Liquid lens 36a works based on the electro-wetting phenomenon described below: a drop of water 103 is deposited on a substrate made of metal, covered by a thin insulating layer. The voltage applied to the substrate generates an electrostatic pressure to force the liquid to change its shape so as to modify the contact angle at the liquid interface. Two iso-density liquids are employed in the liquid lens: one is an insulator such as oil 101 while the other is a conductor such as water 103. The variation of voltage leads to a change of curvature of the liquid-liquid interface 115, which in turn leads to a change of optical power or refraction of the lens. Generally, the two liquid components of the liquid lens are immiscible and have different optical indices. The relative shape of the interface between liquids determines the refractive properties of the lens. The relative indices of refraction of the two liquids must differ from each other by some amount in order to provide adjustable refraction.

Figure 3:
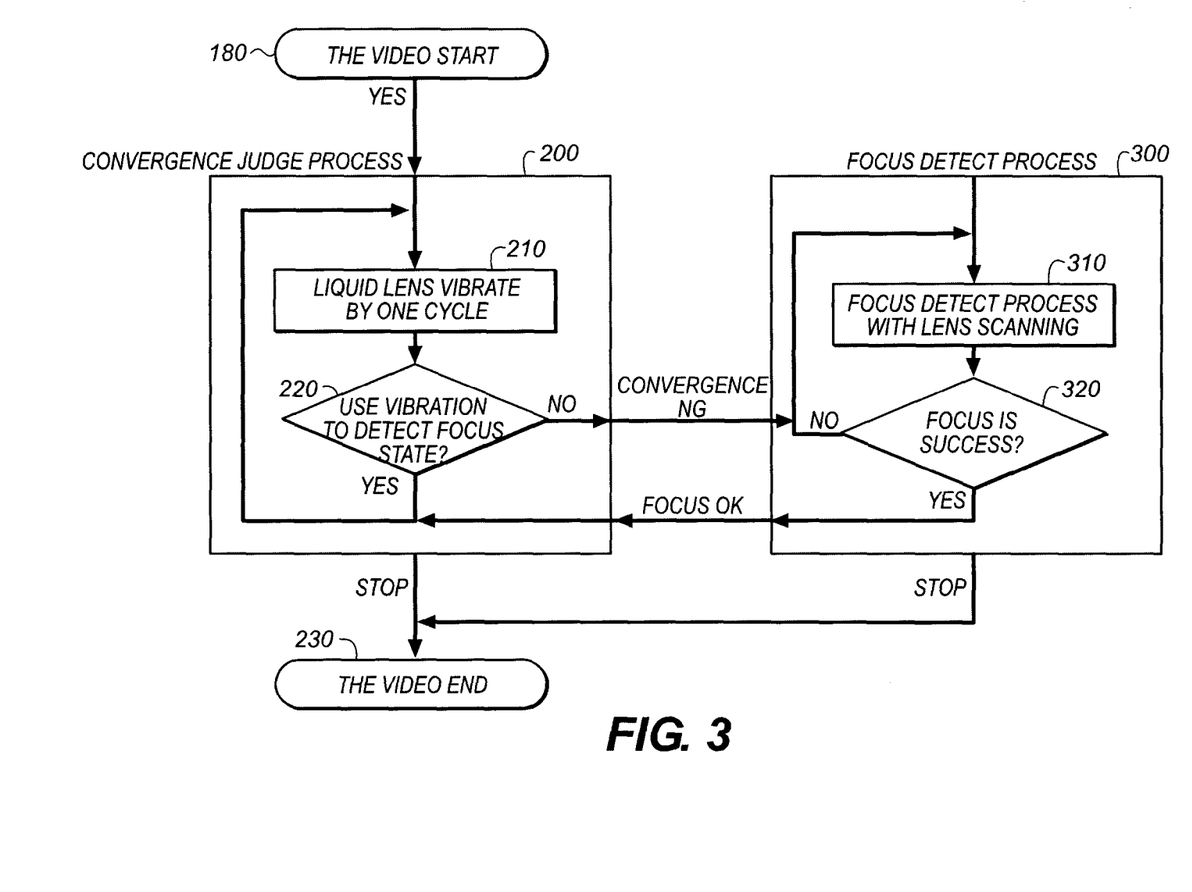
FIG. 3 is a logic flow diagram that shows an autofocus sequence.

FIG. 3 is a logic flow diagram that shows steps in an autofocus sequence. The autofocus method has two states: a convergence testing state 200 and a refocusing state 300. In a startup step 180, the intraoral camera 10 is energized and begins to capture image frames. In a vibration cycling step 210, the liquid lens is vibrated or modulated, rapidly changing the lens shape so that the lens has three focal positions. An image is captured for each vibration position of the liquid lens. A focus detection step 220 then executes, in which the focus of each captured image is measured and the relative focus at each vibration position is analyzed, as described in more detail later. If convergence testing shows that focus is acceptable, autofocus terminates at a termination step 230. If convergence testing shows that focus needs adjustment, refocusing state 300 is executed. In refocusing state 300 a hill-climbing method is used to adjust lens position as part of a lens scanning step 310, to detect the peak value, and to determine its corresponding focus position. A focus assessment step 320 determines whether to repeat lens scanning step 310 or to return to convergence testing state 200. Each of the steps in convergence testing state 200 and refocusing state 300 can be repeated any number of times, as needed.

Figure 4A:
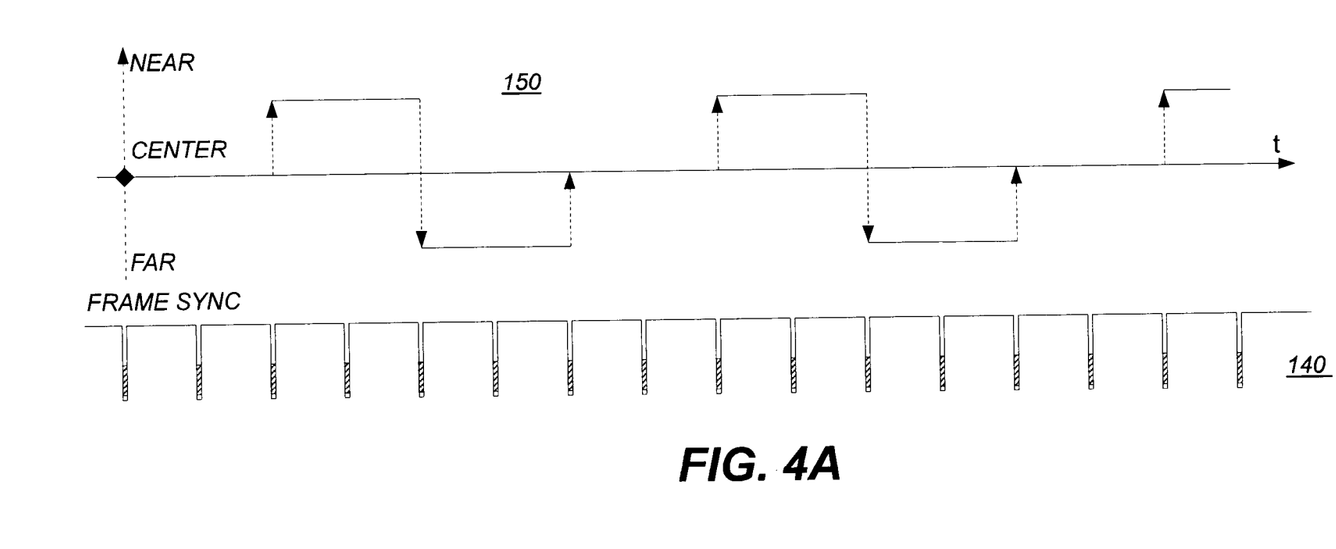
FIG. 4A is a timing diagram that shows a portion of the autofocus detection sequence for a rolling shutter imager.
Figure 4B:
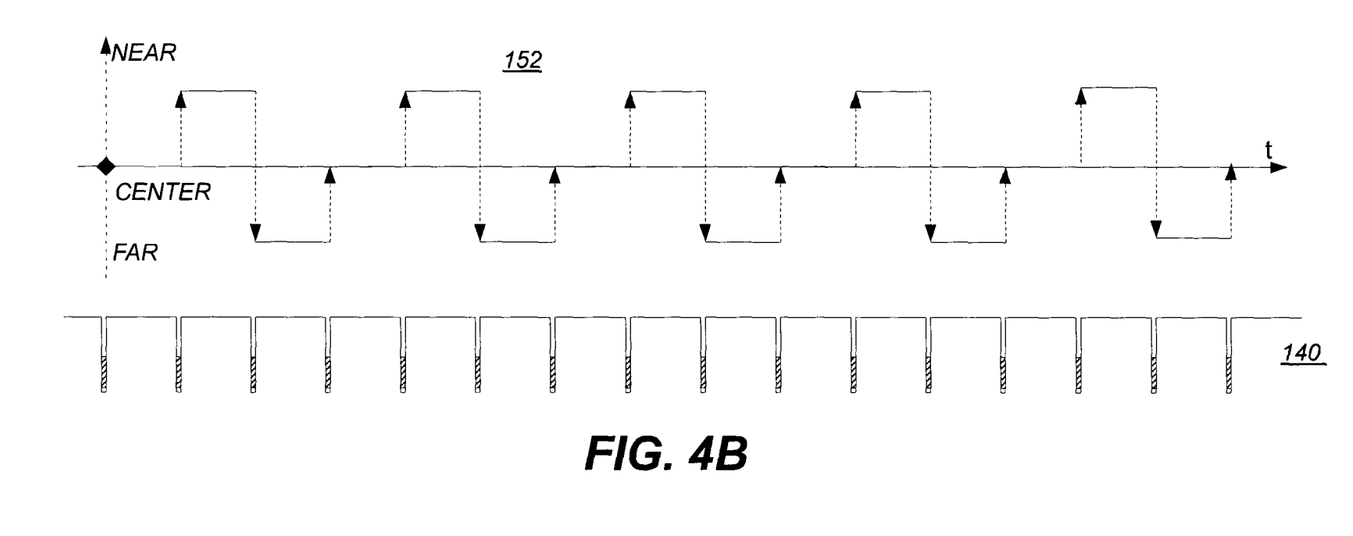
FIG. 4B is a timing diagram that shows a portion of the autofocus detection sequence for a global shutter imager.

To detect focus state and decide focus direction, the liquid lens is rapidly modulated to provide slight vibration, with the cycle timing demonstrated in FIGS. 4A and 4B. In FIG. 4A, the timing sequence is shown for a sensor that has a rolling shutter, such as a conventional CMOS (Complementary Metal-Oxide Semiconductor) sensor. A frame sequence 140 shows the timing of image capture frames for the sensor in rolling shutter mode. An imaging sequence 150 shows the three positions of the liquid lens used for obtaining an image. The three positions that form a single cycle are center, near, and far offset positions, each with a different focus. A suitable value is chosen for the amplitude of the lens focus change to each of the three near, center, and far positions. As shown in the timing diagram, the change in liquid lens position is executed between image capture frames. Each image capture sequence in the cycle spans two image capture frames for the rolling shutter device. The full cycle thus spans six image capture frames.

In FIG. 4B, the timing sequence is shown for a sensor that has a global shutter, such as a conventional CCD (Charge-Coupled Device) sensor. A frame sequence 140 shows the timing of image capture frames for the sensor in global shutter mode. An imaging sequence 152 shows the cycle of three positions of the liquid lens used for obtaining an image with global shutter timing. Again, positions in each cycle are center, near, and far offset positions, each with a different focus. As shown in the timing diagram, the change in liquid lens position is executed between image capture frames. Each image capture sequence in the cycle spans a single image capture frame for the global shutter device. The full cycle thus spans three image capture frames.

Figure 5A:
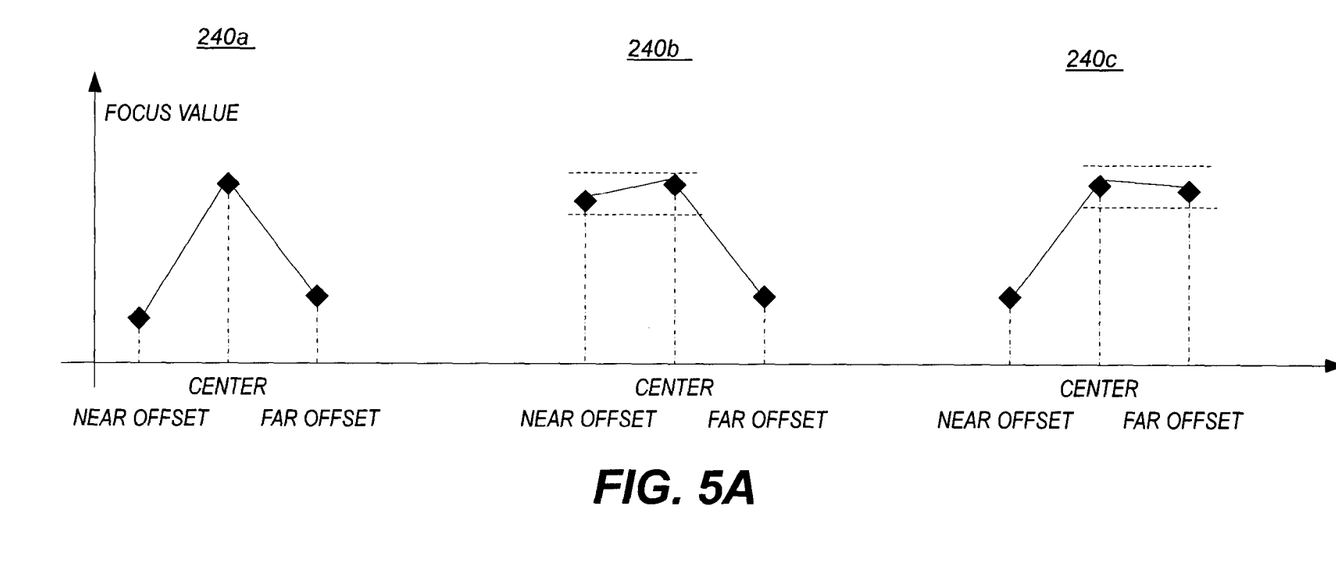
FIG. 5A shows autofocus test results when the liquid lens position is in focus.

The diagram of FIG. 5A shows autofocus test results from convergence testing state 200 of FIG. 3 when the liquid lens position is in focus. Focus is represented on the vertical axis. Focus in the captured image can be measured in a number of ways, such as by analyzing contrast and high frequency components extracted from the image. Graphs 240a, 240b, and 240c are shown. When in focus, the center value is not less than either of the near and far offset values and preferably exceeds the near or far offset values.

Figure 5B:
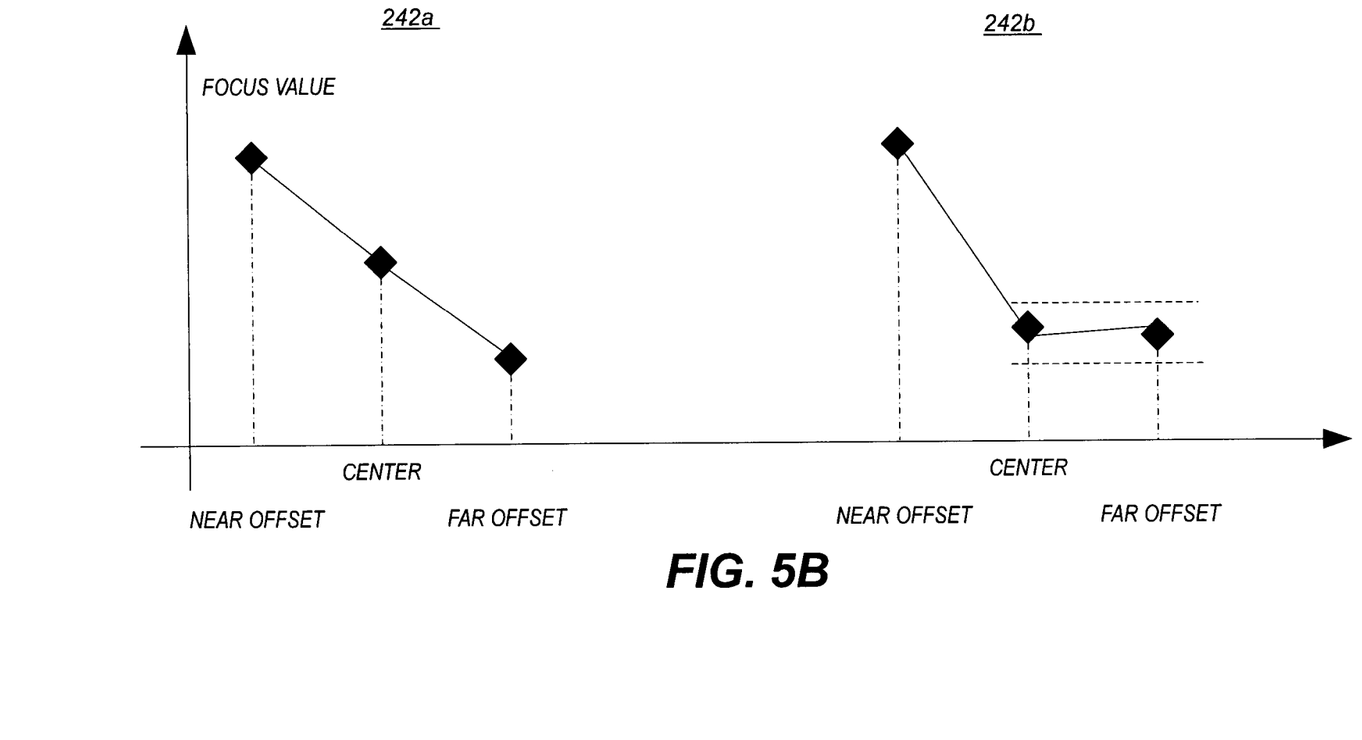
FIG. 5B shows autofocus test results when the liquid lens position is out of focus in one direction.

FIG. 5B shows graphs 242a and 242b that show autofocus test results when the liquid lens position is out of focus in a near-scanning direction. The near offset value exceeds both center and far offset values.

Figure 5C:
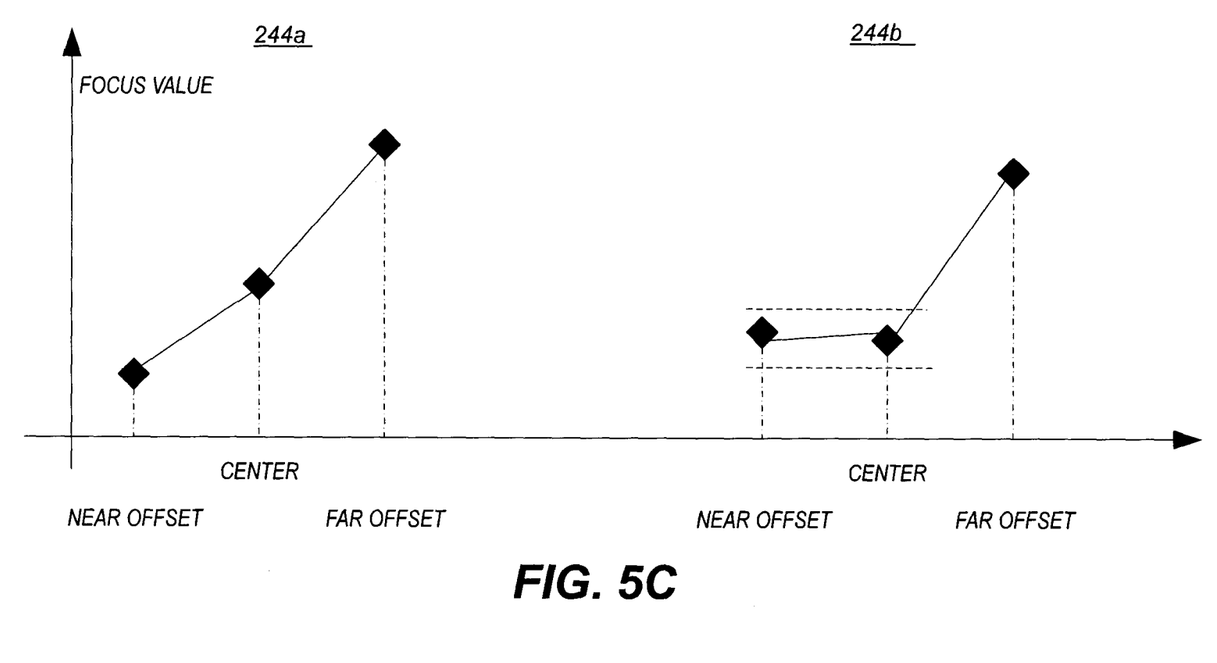
FIG. 5C shows autofocus test results when the liquid lens position is out of focus in the opposite direction from that of FIG. 5B.

FIG. 5C shows graphs 244a and 244b that show autofocus test results when the liquid lens position is out of focus in the opposite direction from that of FIG. 5B. Here, the liquid lens position is out of focus in a far-scanning direction. The far offset value exceeds both center and near offset values.

Figure 5D:
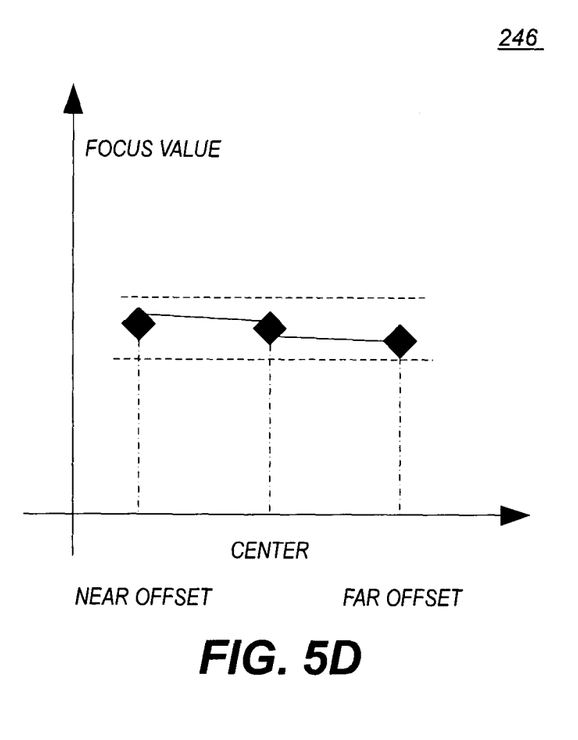
FIG. 5D shows autofocus test results when the liquid lens position is out of focus, with its re-focus direction dependent on the current lens position.

FIG. 5D shows a graph 246 with autofocus test results when the liquid lens position is out of focus, with its re-focus direction dependent on the current lens position.

Figure 5E:
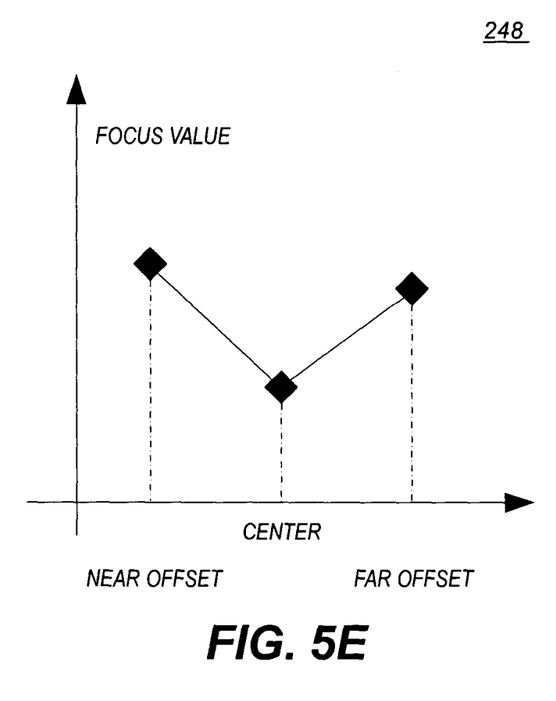
FIG. 5E shows autofocus test results when the liquid lens position is out of focus, with its re-focus direction dependent on the current lens position and on sensed focus values.

FIG. 5E shows a graph 248 with autofocus test results when the liquid lens position is out of focus, with its re-focus direction dependent on the current lens position and on sensed focus values.

The autofocus method of the present invention provides a straightforward method for automatic measurement of focus and adjustment of liquid lens state and position. External devices or measurements are not needed to achieve the needed focus position for intraoral imaging.

Illumination system 11 (FIG. 1) is configured to direct light from a light source in order to illuminate the tooth or other target for improved imaging at imaging sensor 16. The light source can be one or more light emitting diodes (LEDs) or any other known light source. Illumination system 11 can be integrated into the intra-oral camera 10 package or can be provided from a separate device. An optical fiber or other light guide could be provided for directing illumination toward target 1 from an external light source.

Imaging sensor 16 records the image of the target tooth at a fixed position. Imaging sensor 16 can be a complementary metal-oxide-semiconductor (CMOS) device, charge coupled device (CCD), or any other known sensor array type.

Though intra-oral camera 10 of the present invention is designed for imaging an intra-oral target, this device may be used in other suitable applications, particularly where the camera width requirement is fairly constrained, such as for endoscope applications.

The invention claimed is:

1. An autofocus method for an intra-oral camera comprising:
    modulating the focus of a liquid lens in a cycle that has at least first, second, and third focus positions;
    obtaining an image at each focus position and measuring focus of the obtained image;
    adjusting the position of the liquid lens along an optical path of the intra-oral camera according to the measured focus; and
    repeating steps of modulating the focus of the liquid lens in the cycle with at least first, second, and third focus positions, and obtaining the image at each focus position and measuring focus of the obtained image,
    wherein adjusting lens position comprises adjusting lens position in one direction when the focus of the image at the first position exceeds the focus of the image at the second position and adjusting lens position in the opposite direction when the focus of the image at the third position exceeds the focus of the image at the second position, where the second position is in between the first position and the third position,
    where adjusting lens position in one direction and the opposite direction comprises changing a linear position of the liquid lens along an optical axis.

2. The autofocus method of claim 1 wherein obtaining an image at each focus position comprises obtaining an image from a complementary metal-oxide semiconductor sensor.

3. The autofocus method of claim 1 wherein obtaining an image at each focus position comprises obtaining an image from a charge-coupled device sensor.

4. The method of claim 1 wherein the first position is a near offset position, the second position is a center position, and the third position is a far offset position.

5. The method of claim 1 wherein the measured focus is based on brightness of the obtained image.

6. The method of claim 1 wherein modulating the focus of the liquid lens comprises applying first, second, and third voltage levels.

7. An autofocus method for an intra-oral camera comprising:
    modulating the focus of a liquid lens in a cycle that has at least first, second, and third focus positions by applying corresponding first, second, and third voltages to the liquid lens;
    obtaining an image at each of the first, second, and third focus position and measuring focus of the obtained image at each position;
    adjusting the position of the liquid lens along its optical axis according to the measured focus; and
    repeating, one or more times, steps of modulating the focus of the liquid lens in the cycle with at least first, second, and third focus positions, and obtaining the image at each focus position and measuring focus of each obtained image by measuring image contrast, where adjusting the position of the liquid lens comprises moving the position of the liquid lens along an optical path of the intra-oral camera.

8. The method of claim 7 wherein obtaining the image at each of the first, second, and third focus positions comprises obtaining the image in a rolling shutter mode.

9. The method of claim 7 wherein obtaining the image at each of the first, second, and third focus positions comprises obtaining the image in a global shutter mode.

* * * * *